United States Patent [19]

Ofosu-Appiah

[11] Patent Number: 5,695,785

[45] Date of Patent: Dec. 9, 1997

[54] KIDNEY EXTRACT FOR TREATMENT OF SYSTEMATIC LUPUS ERYTHEMATOSUS

[75] Inventor: William Ofosu-Appiah, New Hartford, N.Y.

[73] Assignee: Masonic Medical Research Laboratory, Utica, N.Y.

[21] Appl. No.: 670,527

[22] Filed: Jun. 27, 1996

[51] Int. Cl.$^6$ ................................................. A61K 35/23
[52] U.S. Cl. .................................................... 424/558
[58] Field of Search .................................... 424/558

[56] References Cited

U.S. PATENT DOCUMENTS

| | | | |
|---|---|---|---|
| 3,282,788 | 11/1966 | Daniels et al. | 424/558 |
| 3,676,551 | 7/1972 | Thuillier | 424/558 |
| 3,683,070 | 8/1972 | Thuillier | 424/558 |
| 5,268,382 | 12/1993 | Bartlett et al. | 514/378 |
| 5,560,936 | 10/1996 | Kador et al. | 424/558 |

OTHER PUBLICATIONS

Yves Borel et al., "Prevention of Murine Lupus Nephritis by Carrier–Dependent Induction of Immunologic Tolerance to Denatured DNA", *Science*, 182:76–78.

Lewis P. Parker et al., "Modification of NZB/NZWF$_1$ Autoimmune Disease by Development of Tolerance to DN", *The Journal of Immunology*, 113:292–297.

Yves Borel et al., "Treatment of Lupus Nephritis in Adult (NZB+NZW)F$_1$ Mice by Cortisone–Facilitated Tolerance to Nucleic Acid Antigens", *The Journal of Clinical Investigation*, 61:276–286.

*Primary Examiner*—Jean C. Witz
*Attorney, Agent, or Firm*—Darby & Darby

[57] ABSTRACT

The invention is directed to a method of treating systematic lupus erythematosus (SLE) in animals, including humans, by the oral administration of kidney extracts to decrease anti-DNA antibody production. The method of the invention includes both prophylactic and therapeutic measures.

5 Claims, 1 Drawing Sheet

KIDNEY EXTRACT FOR TREATMENT OF SYSTEMATIC LUPUS ERYTHEMATOSUS

FIELD OF THE INVENTION

The present invention relates to a method of treating systematic lupus erythematosus (SLE) in mammals. Specifically, the present invention provides the oral administration of kidney extracts for the prophylactic and therapeutic treatment of SLE.

BACKGROUND OF THE INVENTION

Systemic lupus erythematosus is an autoimmune disease which is not specific to any organ. This disease affects a large number of organs and has a chronic course with acute episodes. The external manifestations of SLE are lesions on the facial skin. In most cases, other areas of skin and the mucosa are affected. Also observed are nephritis, endocarditis, hemolytic anemia, leukopenia and involvement of the central nervous system.

Many immunological phenomena have been observed with SLE. For example, the formation of antibodies against certain endogenous antigens has been seen. These antibodies are directed against, for example, the basement membrane of the skin, and against lymphocytes, erythrocytes and nuclear antigens. Antibodies which are directed against double-stranded DNA (ds-DNA) form with the latter complexes. These antibodies, together with complement, are deposited on small blood vessels and frequently result in vasculitis. These deposits are especially dangerous when they occur in the renal glomeruli because they result in glomerulonephritis and kidney failure. The incidence of clinically detectable kidney involvement is reported in the literature to be between 50 and 80%.

Glucocorticoids and other immunosuppressive medicaments such as cyclophosphamide (CPA), are of crucial importance for the survival of patients with systemic lupus erythematosus. There is as yet no specific curative agent. To date, therapy has been aimed at preventing or overcoming acute exacerbation and averting recurrences. Patients are generally treated with glucocorticoids and other immunosuppressants. These agents, however, have hazardous side effects.

A variety of animal models have been used to study human SLE. A few strains of mice spontaneously develop SLE, such as NZB X NZW F1 hybrid mice (these animals originated from the Jackson Laboratories, Bar Harbor, Me.). These animals are reared in animal rooms under specific pathogen-free (SPF) conditions.

Previous studies have suggested various methods by suppressing anti-dsDNA autoantibody production in mammals.

Borel et al. (1973) *Science*, 182:76–78 described preventing murine lupus nephritis by neonatal subcutaneous administration of nucleosides (adenosine, guanosine, cytidine and thymidine) conjugated to isogeneic IgG. Borel found that nucleosides covalently bound to autologous IgG prevented the formation of antibody to denatured DNA in mice that were genetically predisposed to produce this antibody. Five of the eight mice rendered tolerant to denatured DNA failed to develop glomerulonephritis after administration of the nucleoside-IgG was stopped. These studies, however, did not determine whether murine SLE could be suppressed in animals that have already formed antibody to denatured DNA.

Parker et al. (1974) *J. Immunol.*, 113:292–297 disclosed suppressing autoimmune diseases by neonatal intraperitoneal administration of DNA coupled to poly-D-lysine. Parker found that mice genetically predisposed to autoantibody formation that received a prolonged high dose administration of SDNA-poly-D-lysine from birth lived significantly longer than the controls.

Borel et al. (1978) *J. Clin. Invest.* 61:276–286 described treating lupus nephritis by intraperitoneal and/or intravenous administration of cortisone, cortisone with toleragen or cortisone with isologous IgG free of nucleosides. Borel found that tolerance to nucleic acid antigens facilitated by cortisone reduced the effects of lupus nephritis.

Clinical trials in human SLE have demonstrated that antigen nonspecific immunosuppression with drugs such as prednisone and azathioprine affect the course of SLE. The current therapy for SLE, however, has several drawbacks. The administration of immunosuppressive drugs does not cure SLE and is associated with drug-related toxicities. One of the primary goals for the immunotherapy of autoimmune diseases is to find nontoxic antigen-specific therapies that can be administered early in the course of the disease.

SUMMARY OF THE INVENTION

The present invention provides methods for the treatment and suppression of systematic lupus erythematosus (SLE) in a mammal by the oral administration of kidney extracts in an amount effective to treat and suppress SLE. Both the clinical and histological effects of SLE are suppressed in a dose-dependent manner by the methods of this invention.

According to the method of this invention, the oral administration of kidney extracts decreases anti-DNA production in animals with SLE. The oral administration of kidney extracts represents an effective, simple and non-invasive method by which an autoimmune disease can be naturally immunoregulated.

DETAILED DESCRIPTION OF THE INVENTION

Definitions

Figure 1:
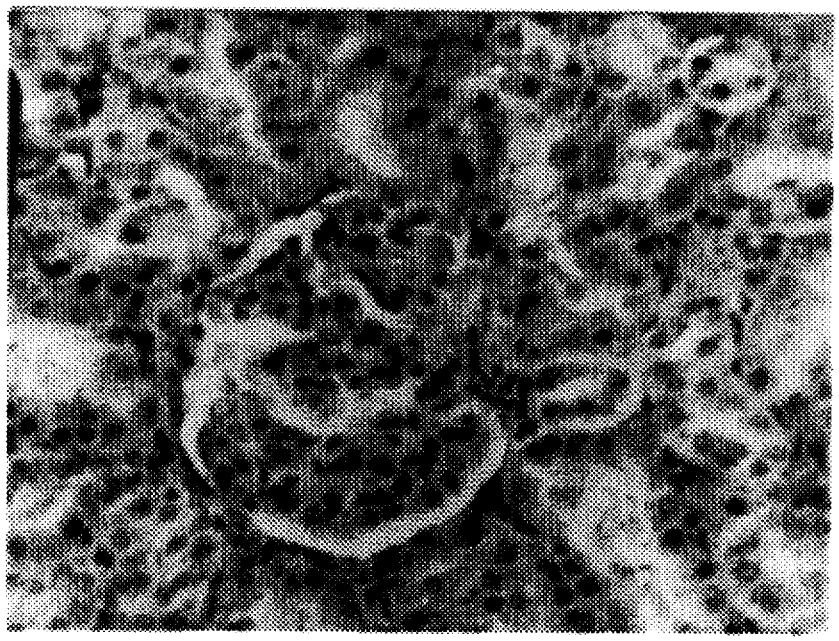
FIG. 1 is a photograph showing the histology of kidneys of NZB/NZW F1 mice fed with PBS. The photo shows inflammatory cells present in both the glomerulus and the surrounding tissues and a loss of the integrity of the glomerulus.

In order to provide a clear and consistent understanding of the specification and claims, including the scope to be given to such terms, the following definitions are provided.

Autoimmune Disease

An autoimmune disease is a malfunction of the immune system of animals, including humans, in which the immune system fails to distinguish between foreign substances within the animal and substances which are part of the animal's normal composition.

Autoantigen

An autoantigen is any substances normally found within an animal that, in an abnormal situation such as an autoimmune disease, is no longer recognized as part of the animal itself by the lymphocytes or antibodies of that animal, and is therefore attacked by the immunoregulatory system as though it were a foreign substance.

Animal

The term animal includes all life forms that have an immunoregulatory system and are therefore susceptible to SLE, including humans.

Administration

The term administration or introduction of a kidney extract to an animal with SLE is intended to describe providing a kidney extract to an animal in a manner which retains the therapeutic effectiveness of the kidney extract for a length of time sufficient to provide a desired beneficial effect to such subject. In a preferred embodiment, the kidney extract is introduced orally. The term oral, however, is not limited to administration provided per os and is intended to include any administration which provides the kidney extract into the animal's stomach or digestive tract.

Kidney Extract

Kidney extracts are proteins collected from the homogenized kidney as described in Example I.

Systemic Lupus Erythematosus (SLE)

SLE is an autoimmune disease which is a chronic inflammatory disease that affects a large number of systems in the body. The pathophysiology of the disease includes severe vasculitis, renal involvement, and lesions of the skin and nervous system. Many immunological phenomena result from the disease including the formation of antibodies against various endogenous antigens such as lymphocytes, erythrocytes and nuclear antigens.

Treatment

The term treatment includes both the prophylactic measures to prevent SLE as well as the suppression or alleviation of symptoms after the onset of SLE.

The present invention relates to the treatment of SLE in animals by the oral administration of kidney extracts. This invention is based on the discovery and confirmation that the oral or enteral administration of kidney extracts is an effective means of decreasing anti-DNA antibody production in animals, thereby inducing the suppression of immune responses to SLE. For example, as demonstrated below, lymphocytes obtained from spleens of mice fed with kidney extract produced significantly less anti-DNA antibody in culture compared to control SLE mice fed with PBS alone. In a preferred embodiment, the kidney extract is administered per os.

In general, kidney extracts are introduced orally in an amount of from 0.1 mg to 3.5 grams per day, and may be administered in single dose form or multiple dose form. Preferably the kidney extract is administered in an amount of from 0.5 to 1.0 mg per day. The individual oral dosage of the kidney extract may range from 0.1 mg to 3.5 grams and preferably 1.0 mg. As is understood by one skilled in the art, the exact dosage is a function of the age, sex and physical condition of the patient, as well as other concurrent treatments being administered. Such preparations may be administered to an animal in need of treatment for SLE as to ameliorate, relieve, alleviate, reverse or lessen the severity of the disease. Such preparations may also be administered to an animal who is predisposed to developing SLE to prevent SLE or lessen the severity of the disease.

When the kidney extract is introduced orally, it may be mixed with other food forms and consumed in solid, semi-solid, suspension, or emulsion form. The extract may be mixed with pharmaceutically acceptable salts, carries, flavor enhancers, and the like.

Kidney extracts may be administered from more than one species or from more than one tissue source. The kidney extracts of this invention may also be administered with any appropriate pharmaceutical carrier to a subject in need of the kidney extracts. Extracts can be administered in any form that effects prophylactic, palliative, preventative or curing conditions of SLE in animals and in particular, humans. For example, kidney extracts can be employed in dosage forms such as tablets, capsules, powder packets, or liquid solutions for oral administration as long as the biological activity of the kidney extract is not destroyed by such dosage form.

Preparations of the kidney extract can be provided as dry powders, food-stuff, aqueous or non-aqueous solvents, suspensions or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose or fixed oils.

Where the kidney extract is administered enterally, it may be introduced in solid, semi-solid, suspension or emulsion form and may be compounded with any of a host of pharmaceutically acceptable carriers, including water, suspending agents and emulsifying agents.

The kidney extracts of the invention may also be administered in sustained release form, especially when administered as a preventive measure, so as to prevent the development of SLE in a subject or when administered to ameliorate or delay SLE.

Pharmaceutical compositions which contain the kidney extracts of the invention and which are useful in the methods of the present invention are manufactured in a manner which is known. For example, the kidney extracts may be provided as a pharmaceutical composition by means of conventional mixing, granulating, dissolving, lyophilizing or similar processes. Such compositions, in and of themselves, find utility in the control of SLE disease.

Additionally, a low potency version of such compositions is useful in the management of mild, chronic, or acute autoimmune disorders.

Kidney extracts which are substantially free of natural contaminants can be isolated and purified from kidneys in accordance with conventional conditions and techniques known in the art such as homogenation, centrifugation, and the like.

Kidney extracts useful in the methods of the invention can be identified by the ability of these extracts to suppress SLE upon administration of the extract to a subject afflicted with or predisposed to SLE. In the methods of the invention, SLE may be suppressed by such administration of kidney extracts either prior to or after appearance of disease symptoms.

In order to further illustrate the present invention, the experiments described in the following experiments were carried out. It should be understood that the invention is not limited to the specific example or the details described therein. The results obtained from the experiments described in the example are shown in the accompanying figures and tables.

EXAMPLE

Preparation of Kidney Extracts

Kidneys were aseptically removed from 4 young (4 week old) NZB/W mice, (Jackson Laboratories, Bar Harbor, Me.) minced with scissors and then suspended in 10 ml of phosphate-buffered saline (PBS). The kidneys were then mechanically homogenized with an electric homogenizer until no intact cells could be observed by phase microscopy. The homogenate was sonicated for 10 minutes at 140 Watts using a Biosonic III Sonicator and then centrifuged for 60 minutes at 100,000 g in an ultracentrifuge (Beckman L8-M) at 4° C. The resulting supernatant was harvested and used as the kidney extract. After determining the protein concentration using the Bio-Rad Protein assay described by Bradford, M. M. (1976) "A rapid and sensitive method for the quantitation of microgram quantities of protein utilizing the principle of protein-dye binding", *Analytical Biochem.* 72:248–254 which is incorporated herein by reference, the supernatant was aliquoted at 2 mg/ml and lyophilized. For use in oral feeding, an aliquot of the lyophilized material was reconstituted with 1 ml sterile phosphate buffer saline (PBS).

Induction of Oral Tolerance to Kidney Extracts

Young NZB/W F1 mice (4 week old) were fed 500 µg of kidney extract three times weekly for 4 weeks in 0.2 ml phosphate buffered saline (PBS) by using a 22-gauge stainless steel ball-tipped feeding needle. These mice did not exhibit clinical signs of SLE, however, NZB/W F1 mice are predisposed to developing SLE. Control mice received PBS alone. Two months after the last feeding, the animals were sacrificed by ether inhalation and cervical dislocation. Their spleens, blood and kidneys were subsequently removed for analysis.

Lymphocytes were prepared from the spleens using the techniques described by W. Ofosu-Appiah, C. Ruggiero and Huang L. Y. (1993) "Isolation of T cell clones with specificity for Aortic arterial antigen from spontaneously hypertensive rats". *J. Hypertens*, 11:1319–1328, which in incorporated herein by reference. The lymphocytes were cultured in vitro for anti-DNA antibody production by co-culturing these cells with purified T-cells and B-cells from spleens of kidney extract-fed and PBS-fed mice.

Sera were prepared from clotted blood by centrifugation at 3000 rpm (1,800 g). The sera were used to measure the level of anti-DNA antibodies as described below.

The kidneys were placed in formalin for histological analysis.

As shown in Table 1, there was significant suppression of IgG anti-DNA antibody production in animals fed 500 µg of kidney extract (KE). Specifically, sera obtained from mice fed with kidney extract showed significantly lower anti-DNA antibody levels compared to mice fed with calf thymus DNA or control mice fed with PBS alone.

Figure 2:
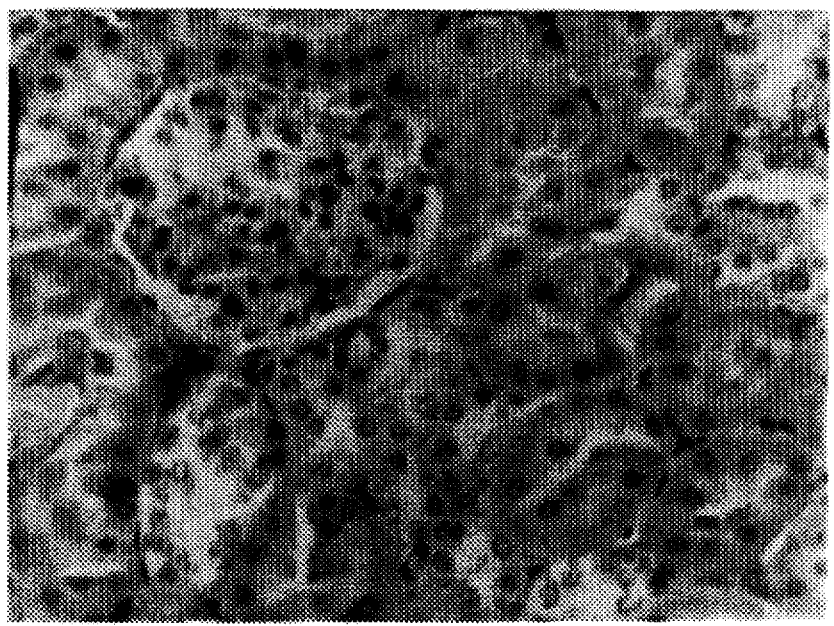
FIG. 2 is a photograph showing the histology of kidneys of NZB/NZW F1 mice fed ICE. The photo shows inflammatory cells present in the glomerulus only.

Histological examination showed more inflammatory cells in both the glomerulus and the surrounding tissues in the mice fed with PBS (FIG. 1) than mice fed with KE (FIG. 2), where the inflammatory cells appeared to be confined to the glomerulus. Another histological difference between mice fed with PBS and KE was that in the PBS-fed mice the integrity of the glomerulus was lost whereas in the KE-fed mice, the integrity of the glomerulus was maintained even though there are inflammatory cells present in the glomerulus.

Production of Autoantibodies in vitro

T cells from the spleen ($2\times10^6$/well) were cultured with $2\times10^6$/well B cells from the spleen (plus macrophages) in 1 ml RPMI 1640 medium supplemented with 10% FBS, $5\times10^{-5}$M 2-mercapto ethanol (2-ME) and antibiotics in 24-well plates (Costar, Cambridge, Mass.). The antibiotic used was Gentamicin (50 mg/ml). The cells were grown at 37° C. After 7 days in culture, the supernatants were harvested by centrifugation as described by Mohan, C. S.; Adams, S.; Stanik, V. and Datta, S. K. (1993) "A major immunogen for pathogenic autoantibody-inducing T cells of lupus", *J. Exp. Med.*, 177:1367–1381. Subsequently, the supernatants were purified by 47% saturated ammonium sulfate (SAS) precipitation and dialyzed against PBS as described by Mohan et al. The supernatants were stored at −70° C. until assayed.

Assay of IgG Anti-DNA Antibodies

IgG class antibodies to double-stranded DNA (dsDNA) produced in the culture supernatants were measured by ELISA. Immulon 2 flat bottom microtiter plates (Dynatech, Alexandria, Va.) were coated overnight at 4° C. with 0.01% methylated bovine serum albumin (mBSA) (Sigma Chemical Co., St. Louis, Mo.) in 50 mM carbonate buffer at pH 9.6. Calf thymus DNA (Sigma Chemical Co.) was dissolved in 33 mM sodium acetate, 50 mM sodium chloride and 0.03 mM zinc chloride. This solution had a pH of 4.5 and was filtered through a 0.45 µm nitrocellulose filter (Millipore Corp., Bedford, Mass.) to remove ssDNA. The DNA solution was used for coating plates as dsDNA. The plates were flicked dry prior to adding 100 µl (100 µg/ml) of the DNA solution in each well. The plates were washed three times with phosphate buffer saline (PBS) containing 0.05% Tween 20 and 0.5% bovine serum albumin (BSA). Excess binding sites were blocked with 2% BSA in PBS for 1 hour at 37° C. The plates were washed three times with PBS-Tween.

The dsDNA-mBSA coated plates were then incubated in duplicate with serial dilutions of SAS-precipitated culture supernatants (SAS-CS) in PBS containing 0.05 % Tween 20 and 0.5% BSA or serum diluted 1:100 overnight at 4° C. Duplicate dilutions SAS-CS or sera were also incubated in parallel mBSA-coated wells that did not contain dsDNA. The values of binding in these control wells were subtracted from the values of binding in dsDNA wells. The plates were washed to remove unbound IgG. The amount of specific antibody bound to either dsDNA was determined by incubation with 100 µl of an optimum dilution of goat anti-mouse IgG (BioProducts for Science, Indianapolis, Ind.) covalently linked to alkaline phosphatase for 1 hour at 37° C. After washing three times with buffer, bound enzyme was quantified by addition of 200 µl of p-nitrophenylphosphate, the chromogen substrate, at 1 mg/ml in 10% diethanolamine buffer and incubation at 37° C. for 30 minutes. The reaction was stopped with 50 µl of 3M NaOH and the plates read at 405 nm using an automatic plate reader (Bio-rad Labs, Richmond, Va.).

As shown in Table 1 below, sera obtained from mice fed with kidney extract showed significantly lower anti-DNA antibody levels compared to mice fed with calf thymus DNA or control mice fed with PBS alone. The lymphocyte studies showed that lymphocytes obtained from spleens of mice fed with kidney extract produced significantly less anti-DNA antibody in culture compared to mice fed with PBS alone. Thus, kidney extract administration beginning at an early age appears to be an effective therapy of SLE in animals. Because anti-DNA antibody levels are strongly correlated with SLE disease activity, these results demonstrate that oral administration of kidney extract provides a new approach for the treatment of human SLE.

TABLE 1

Suppression of anti-DNA antibody production in SLE mice by oral administration of kidney extract[a]
Anti-DNA antibody Levels (OD 405 nm)[b]

| Feeding Treatment | Culture Supernatants | Sera |
|---|---|---|
| Control (PBS) | 1.37 ± 0.06 | 1.63 ± 0.11* |
| (N = 10) | (range 1.02–1.57) | (range 1.10–1.99) |
| DNA in PBS | 1.31 ± 0.09 | 1.36 ± 0.07** |
| (from calf thymus) | (range 1.17–1.50) | (range 1.22–1.52) |

TABLE 1-continued

Suppression of anti-DNA antibody production in SLE mice by oral administration of kidney extract[a]
Anti-DNA antibody Levels (OD 405 nm)[b]

| Feeding Treatment | Culture Supernatants | Sera |
|---|---|---|
| (N = 5) | | |
| Kidney extract in PBS (KE) | 0.30 ± 0.06 | 0.53 ± 0.16*** |
| (N = 10) | (range 0.11–0.79) | (range 0.14–1.93) |

[a]Four-week old female NZB/W mice (10 per group) were fed either PBS, DNA or KE, 500 µg per feeding as described in methods. Eight weeks after feeding, lymphocytes were prepared from spleens and cultured in vitro for 7 days. Culture supernatants were harvested, purified by 47% saturated ammonium sulfate (SAS) precipitation, dialyzed against PBS and serially diluted. Sera were diluted 1:100 and IgG anti-DNA antibody levels were determined by ELISA. Results are mean ± SEM. The numbers in parentheses represent the range of values observed.
[b]Levels of anti-DNA Abs at 24 weeks of age.
*P > 0.05, Animals fed with PBS versus animals fed with DNA.
**P < 0.001, Animals fed with DNA versus animals fed with KE.
***P < 0.001, Animals fed with PBS versus animals fed with KE.

What is claimed is:

1. A method for treatment of systemic lupus erythematosus comprising administering a therapeutically effective amount of a pharmaceutical composition comprising a kidney extract to an animal in need thereof.

2. The method of claim 1, wherein said kidney extract is administered orally.

3. The method of claim 1, wherein said kidney extract is administered enterally.

4. The method of claim 1, wherein said therapeutically effective amount of the kidney extract is from about 0.1 mg to about 3.5 gms per day.

5. The method of claim 1, wherein said therapeutically effective amount of the kidney extract is from about 0.5 to about 1.0 mg per day.

* * * * *